(12) United States Patent
Romley et al.

(10) Patent No.: US 7,621,874 B2
(45) Date of Patent: Nov. 24, 2009

(54) SYSTEMS AND METHODS FOR IMPROVED THREE-DIMENSIONAL IMAGING OF A BODY LUMEN

(75) Inventors: Richard Romley, Tracy, CA (US); Thomas C. Pham, San Jose, CA (US); Scott Harshman, Livermore, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 557 days.

(21) Appl. No.: 11/012,663

(22) Filed: Dec. 14, 2004

(65) Prior Publication Data

US 2006/0173299 A1 Aug. 3, 2006

(51) Int. Cl.
*A61B 8/14* (2006.01)
(52) U.S. Cl. .................. 600/463; 600/459; 600/467; 128/916
(58) Field of Classification Search ............ 600/427, 600/437, 443, 447, 466; 128/916, 616
See application file for complete search history.

(56) References Cited

U.S. PATENT DOCUMENTS

| | | | |
|---|---|---|---|
| 5,193,546 A | 3/1993 | Shaknovich et al. | |
| 5,372,138 A * | 12/1994 | Crowley et al. | 600/463 |
| 5,383,454 A | 1/1995 | Bucholz | |
| 5,622,170 A | 4/1997 | Schulz | |
| 5,987,349 A | 11/1999 | Schulz | |
| 6,019,726 A * | 2/2000 | Webb | 600/459 |
| 6,228,028 B1 | 5/2001 | Klein et al. | |
| 6,374,135 B1 | 4/2002 | Bucholz | |
| 6,398,731 B1 | 6/2002 | Mumm et al. | |
| 6,442,416 B1 | 8/2002 | Schulz | |
| 6,490,467 B1 | 12/2002 | Bucholz et al. | |
| 6,592,520 B1 * | 7/2003 | Peszynski et al. | 600/437 |
| 6,593,884 B1 | 7/2003 | Gilboa et al. | |
| 6,685,643 B1 | 2/2004 | Waldinger et al. | |
| 6,785,571 B2 | 8/2004 | Glossop | |
| 6,923,768 B2 * | 8/2005 | Camus et al. | 600/463 |
| 2002/0035321 A1 | 3/2002 | Bucholz et al. | |
| 2002/0042571 A1 | 4/2002 | Gilboa et al. | |
| 2002/0049375 A1 * | 4/2002 | Strommer et al. | 600/407 |
| 2002/0087075 A1 | 7/2002 | Bucholz | |
| 2003/0013958 A1 | 1/2003 | Govari et al. | |
| 2003/0160721 A1 | 8/2003 | Gilboa et al. | |

* cited by examiner

*Primary Examiner*—Eric F Winakur
*Assistant Examiner*—Michael T Rozanski
(74) *Attorney, Agent, or Firm*—Darby & Darby P.C.; Patrick R. Turner

(57) ABSTRACT

The systems and methods described herein provide for the improved three-dimensional imaging of the an internal body lumen of a living being. A medical imaging system is provided which can include an image processing system and a medical imaging device. The medical imaging device can be insertable into the internal lumen and can include an image acquisition system configured to image the lumen and detect the position and orientation of the image acquisition system within the lumen. The image acquisition system can output the image, position and orientation data to the image processing system to be used by the processing system to generate and display a virtual three-dimensional image of the internal lumen to the user. The user can use various software tools provided by the image processing system, such as distance and area measuring tools, to interact with the image.

10 Claims, 8 Drawing Sheets

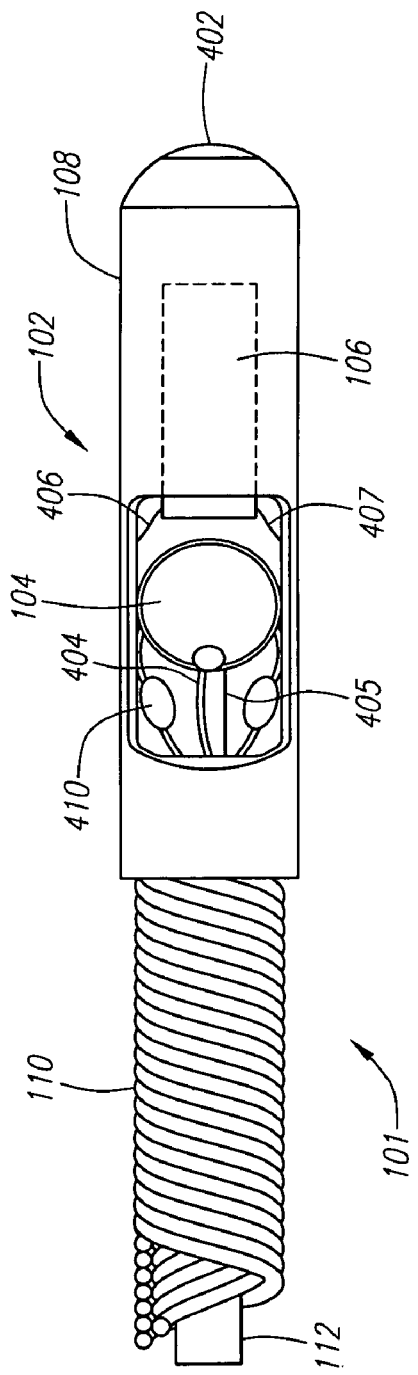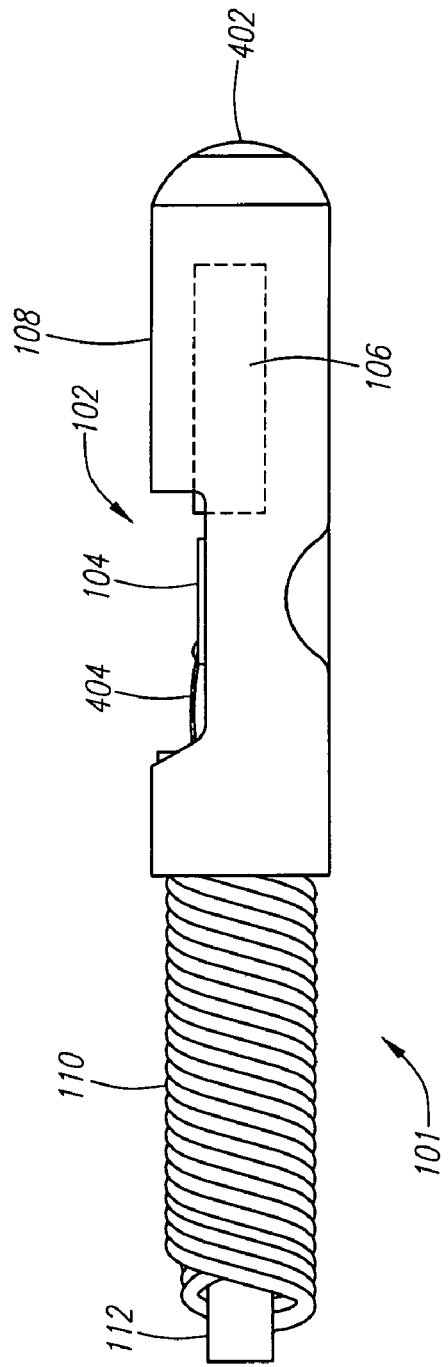

SYSTEMS AND METHODS FOR IMPROVED THREE-DIMENSIONAL IMAGING OF A BODY LUMEN

FIELD OF THE INVENTION

The systems and methods relate generally to the internal imaging of a living being, and more particularly, to the improved three dimensional imaging of a body lumen with an elongate medical device.

BACKGROUND INFORMATION

Conventional medical imaging systems, such as imaging catheters and the like, are capable of imaging the interior of an internal body lumen, such as a blood vessel, in a two dimensional (2D) manner. In 2D imaging, variations in the cross section and width of the body lumen are visible. However, in a three-dimensional (3D) reconstruction, such as reconstructed 3D image 20 of blood vessel 10 depicted in FIG. 1, the lumen itself will appear as being straight or uni-directional, i.e., any curves or bends in the lumen along the length of the lumen are not visible. This is because the lumen is imaged by sliding the imaging device along the length of the lumen while at the same time imaging multiple consecutive cross sections of the lumen. The 3D reconstruction of the lumen is created by merging these multiple cross sections together. However, because the imaging devices are incapable of providing information on the lateral spatial relationship between cross-sections, i.e., whether the position of these cross sections change relative to each other, the 3D reconstruction of the lumen must therefore assume that the lumen is straight and merges the cross sections together accordingly.

Because the presence of bends and curves in the lumen can impact many medical procedures, this limitation significantly reduces the number of diagnostic and therapeutic applications in which 2D imaging systems can be used. For instance, curves, twists and other variations in the 3D structure of a lumen can effect distance and area measurements taken along the lumen. Also, as another example, the degree of success in stent deployment procedures, such as whether the stent was properly deployed along a straight segment of a blood vessel, cannot be readily or efficiently determined.

Accordingly, improved 3D imaging systems are needed that can display the full 3D structure of internal body lumens.

SUMMARY

The systems and methods provided herein allow for the improved 3D imaging of an internal body lumen to display the 3D vascular structure of the lumen. In an example embodiment, a medical imaging system is provided having an elongate medical device configured for insertion into the internal lumen of a living being. The elongate device has an inner lumen configured to slidably receive an imager and a sensor. The imager can be configured to image the internal lumen and output an imaging output signal and the sensor can be configured to sense the position and orientation of the sensor and output a sensor output signal usable to determine the position and orientation of the sensor.

In an example embodiment, the imager is an ultrasound transducer and is coupled with the distal end of an elongate driveshaft insertable into the inner lumen of the elongate medical device. The imager can be housed with the sensor within a housing located on the distal end of the driveshaft. An image processing system can be coupled with a proximal end of the elongate medical device and the imager and sensor can be communicatively coupled with the image processing system with a transmission cable located within the driveshaft. In an example embodiment, the sensor is configured to output a signal usable to determine the position of the sensor in three-dimensional space and the yaw and pitch of the sensor.

In another example embodiment, the medical imaging system can include an elongate medical device having an inner lumen located therein, an image acquisition system and an image processing system. In this embodiment, the image acquisition system is insertable into the inner lumen of the elongate medical device and configured to image the internal lumen. The image acquisition system can also be configured to detect the position and orientation of the image acquisition system within the internal lumen and output at least one output signal usable to display the image and determine the position and orientation of the acquisition system. The image processing system can be communicatively coupled with the image acquisition system and configured to process the at least one output signal. The image processing system can be configured to create a three dimensional image of the internal body lumen based on the at least one output signal.

Also provided herein is a method for three-dimensional imaging of an internal body lumen. An example embodiment of the method includes positioning a distal region of an elongate tubular member within an internal lumen of a living being, where the tubular member has an inner lumen configured to slidably receive an elongate driveshaft. Then, the method includes positioning a distal region of the driveshaft within the distal region of the tubular member and moving the driveshaft along a length of the internal lumen. The method includes imaging the length of the internal lumen with an imaging device coupled with the distal region of the driveshaft and sensing the position and orientation of a sensor coupled with the distal region of the driveshaft while imaging the internal lumen. An external image processing system can be used to generate and display a 3D image of the internal lumen using the imaging, position and orientation data.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments.

FIGS. 4A-B depict schematic top and side views, respectively, of another exemplary embodiment of a medical imaging device.

DETAILED DESCRIPTION

The systems and methods described herein provide improved 3D imaging systems capable of imaging the three dimensional vascular structure of a living being. More specifically, the systems and methods allow a user to advance a medical imaging device through the interior of a body lumen, such as a blood vessel and the like, while at the same time imaging the lumen and detecting the orientation and position of the imaging device. This information can be used to reconstruct a 3D image of the body lumen which can then be used for numerous diagnostic and therapeutic applications.

Figure 1:
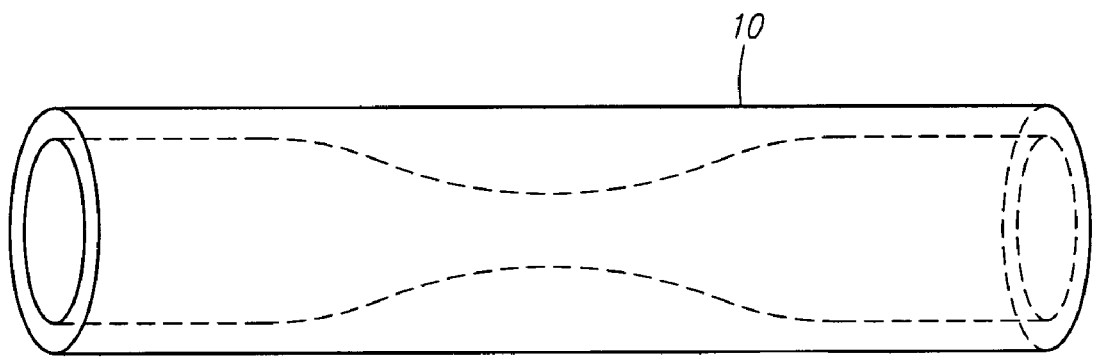
FIG. 1 depicts an example of a conventional 3D reconstructed image of a blood vessel.
Figure 2A:
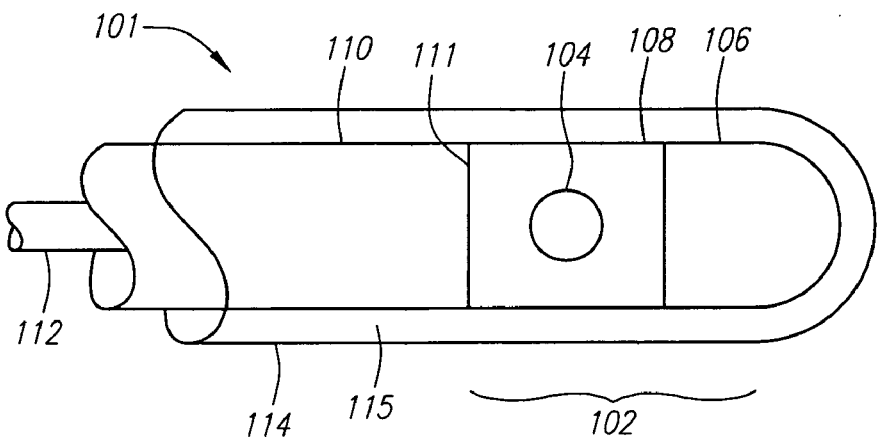
FIG. 2A depicts a cross-sectional view of an exemplary embodiment of a medical imaging device.

FIG. 2A depicts a schematic view of the distal region of a preferred example embodiment of medical imaging system 100. Within medical imaging system 100 is elongate medical imaging device 101 including image acquisition system 102, which in this embodiment includes imager 104 and position and orientation sensor 106 housed within housing 108. Preferably, medical imaging device 101 is an intravascular catheter, although it is not limited to such. The image acquisition system 102 is coupled with the distal end 111 of elongate driveshaft 110 for support. Elongate tubular member 114 is configured to slidably receive image acquisition system 102 and driveshaft 110 within inner lumen 115. Image acquisition system 102 is electrically coupled with the distal end of transmission cable 112, which is preferably a coaxial cable. The proximal end of transmission cable 112 is electrically coupled with image processing system 120 (not shown).

Figure 2B:
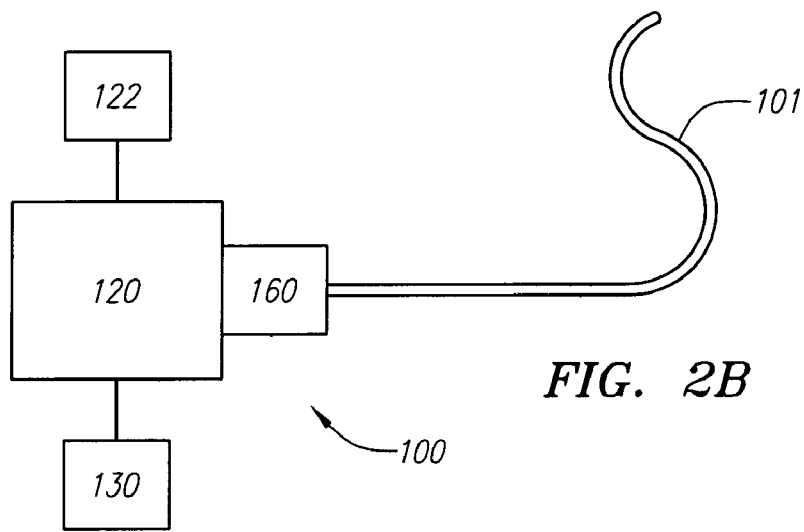
FIG. 2B depicts a schematic view of an exemplary embodiment of a medical imaging system.

FIG. 2B depicts a schematic view of another exemplary embodiment of medical imaging system 100. Here, medical imaging device 101 is coupled with image processing system 120 via proximal connector 160. Proximal connector 160 electrically couples transmission cable 112 with image processing system 120 while at the same time allowing mechanical rotation of transmission cable 112 and driveshaft 110 within elongate tubular member 114. Image processing system 120 is configured to process the image, position and orientation output signals from image acquisition system 102 and reconstruct a virtual 3D image of the internal body lumen. Image processing system is preferably coupled with a graphical user interface (GUI) 122 to display the reconstructed 3D image. If desired for the application, image processing system 120 can be configured to process and display the 3D image in real-time.

Sensor transmitter 130 can also be optionally included within the imaging system 100. Transmitter 130 is preferably used in embodiments or applications where sensor 106 is a passive sensor requiring an external transmit source to transmit a reference signal to aid sensor 106 in detecting it's position and orientation. Passive sensor 106 and transmitter 130 will be discussed in more detail below.

Preferably, imager 104 is an ultrasound imager, such as an ultrasound transducer. In one embodiment, transducer 104 is a single element transducer and medical imaging system 100 can image the interior of the body lumen by rotating driveshaft 110 and transducer 104 located thereon, while at the same time activating the transducer to image the lumen and output an imaging signal to the image processing system via cable 112. In another embodiment, transducer 104 can be a transducer array and imaging system 100 can image the lumen directly without rotation of the driveshaft 110. Imaging device 104 can also be an optical imager such as those used in Optical Coherence Tomography (OCT) systems and Optical Coherence Domain Reflectometry (OCDR) systems and the like.

Figure 3:
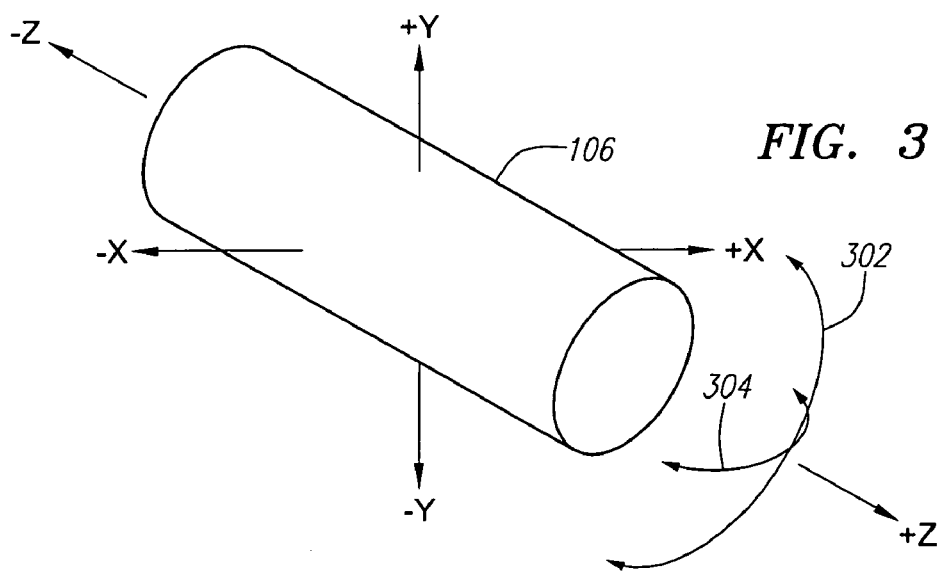
FIG. 3 depicts a perspective view of an exemplary embodiment of a position and orientation sensor.

Position and orientation sensor 106 is preferably configured to detect the position and orientation of sensor 106 during the imaging procedure. In one embodiment, sensor 106 is configured to measure at least five degrees of freedom for sensor 106, as depicted in FIG. 3. FIG. 3 depicts a cylindrical embodiment of sensor 106 as well as five degrees of freedom measured in relation thereto. Sensor 106 can preferably measure the three positional degrees of freedom that are equivalent to movement in each of the three directions X, Y and Z. Sensor 106 is also preferably configured to measure pitch and yaw of sensor 106, indicated by directional arrows 302 and 304, respectively. System 100 preferably does not require the measurement of a sixth degree of freedom referred to as roll (or rotation) because sensor 106 is rotated along with transducer 104 during the imaging procedure. However, other embodiments of system 100, such as optical imaging embodiments that do not involve the rotation of sensor 106, can be configured to measure roll to provide more detail on the vascular structure.

FIGS. 4A and 4B depict top and side schematic views, respectively, of another exemplary embodiment of medical imaging device 101. For example, imager 104 is preferably a transducer. Transducer 104 is not limited to any shape, composition or design and can be configured in accordance with the needs of the application. In this embodiment, position and orientation sensor 106 is cylindrically shaped and located distal to transducer 104 within generally cylindrical housing 108. Sensor 106 can also be located proximal to transducer 104 or in a separate housing as desired. Sensor 106 can be any single sensor or combination of sensors capable of outputting a signal usable to determine the position and orientation of sensor 106 or image acquisition system 102. Although sensor 102 is preferably capable of detecting both position and orientation to maximize the imaging capability of system 100, sensor 106 can also be configured to measure solely position or orientation, or any one or more of the six degrees of freedom described above.

Sensor 106 can operate actively by outputting position and orientation information directly. For instance, sensor 106 can output a wireless tracking signal to a receiver capable of determining the position of sensor 106. Sensor 106 can also include a small gyroscope or equivalent device that can actively measure the orientation of sensor 106. In a preferred embodiment, sensor 106 is configured to operate passively, or in response to an external reference signal. In one exemplary embodiment, passive sensor 106 is a single passive coil, while in another embodiment, sensor 106 is a combination of one or more orthogonally placed coils.

Passive sensor 106 preferably outputs a sensor output signal in response to a transmitted reference signal having a known power propagating from a separate transmitter 130 within system 100. System 100 can be configured such that image processing system 120 controls the transmission of a reference signal from transmitter 130. Preferably, the transmit signal induces a current in the coil(s) present within sensor 106. The current is preferably a function of distance and angle from transmitter 130, allowing the relative position and orientation of sensor 106 to be determined. In embodiments where transducer 104 is rotated to image the lumen, system 100 is preferably configured to determine the radial location of sensor 106, i.e., the position of sensor 106 about the rotational axis, during the position and orientation sensing process. The radial location of sensor 106 can be determined by monitoring the radial position of transducer 104 or of the driveshaft 110 and taking into account any rotational distortion therein. Sensor 106 preferably outputs the induced sensor output signal over transmission line 112, but can also be configured to output the sensor output signal wirelessly.

It should be noted that system 100 incorporated with a tracking sensor 106 has significant advantages over conventional electromagnetic tracking systems. These advantages and differences include, but are not limited to, the ability to image and sense position and orientation at the same or nearly the same time, the ability to sense position and orientation during rotation of driveshaft 110 (for example in embodiments using ultrasound imaging), the ability to be routed within the internal vasculature without a preexisting 3D map of the vasculature and the ability to image narrow vasculature such as coronary veins and arteries, which can be on the order of 2.5 French and below. Conventional tracking systems are too large for insertion into narrow vasculature of this size.

Housing 108 preferably includes a rounded distal tip 402 to prevent damaging elongate tubular member 114. Housing 108 is preferably bonded with flexible driveshaft 110 using adhesives, laser welding, brazing and the like. Housing 108 can be manufactured using laser cutting or machining processes such as mechanical or electric discharge machining processes and the like. Housing 108 is preferably visible to an external imaging device, e.g., radio opaque, in order to allow tracking of housing 108 while in the body. In this embodiment, housing 108 is composed of stainless steel and is gold plated, but housing 108 is not limited to such and any appropriate composition, material or manufacturing process can be used in accordance with the needs of the application.

Driveshaft 110 is preferably fabricated with oppositely wound superelastic coils composed of NITINOL or an equivalent alloy. Again, driveshaft 110 is not limited to any configuration or composition and can be implemented in accordance with the needs of the application. In this embodiment, transducer 104 and sensor 106 each have two electrical connections with transmission cable 112. Transducer connections 404 and 405 as well as sensor connections 406 and 407 are preferably made within housing 108 and are isolated using ultra-violet (UV) cure adhesive 410 or the like.

Figure 5A:
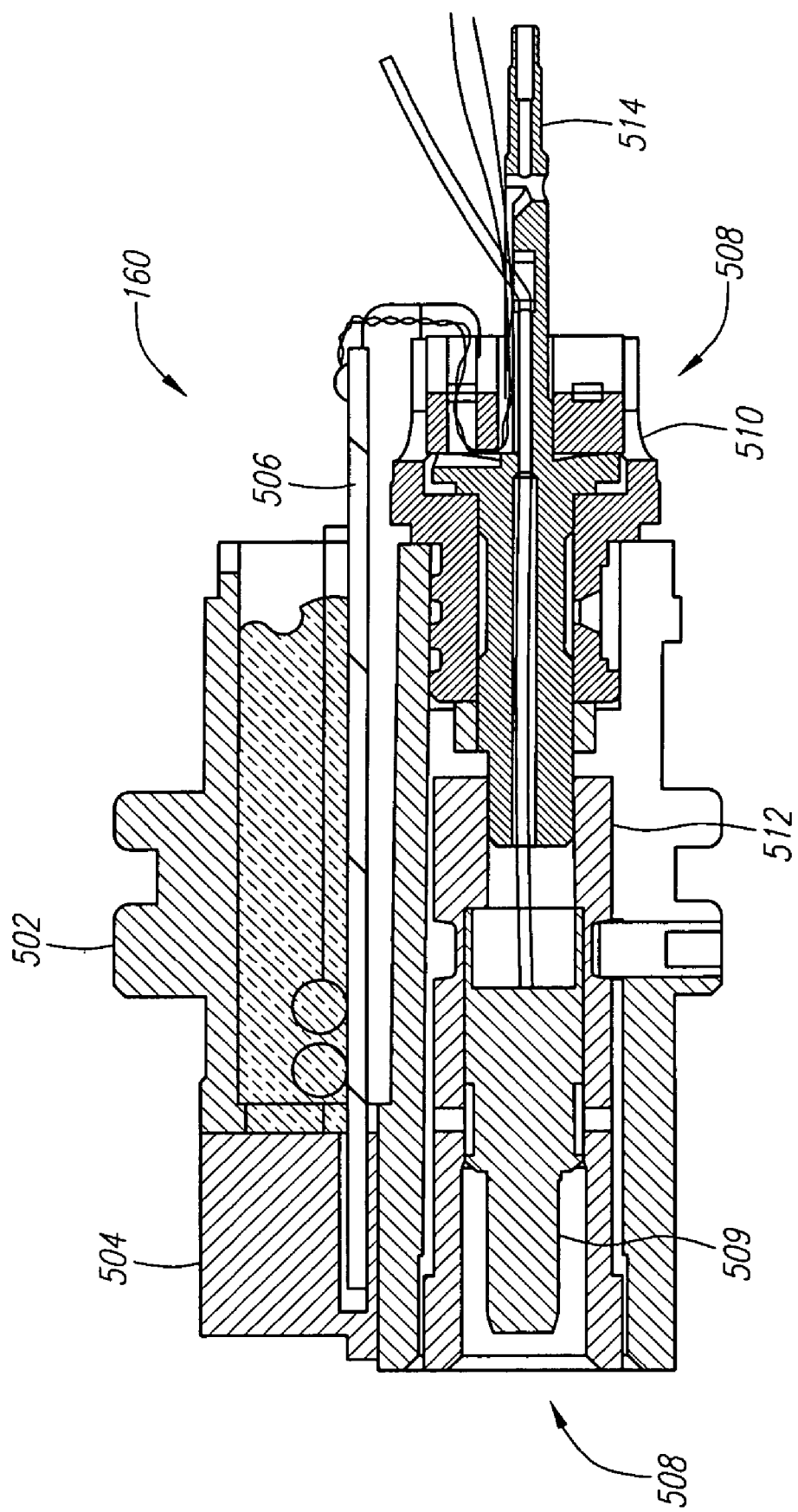
FIG. 5A depicts a schematic view of an exemplary embodiment of a proximal connector.

FIG. 5A depicts an exemplary embodiment of a proximal connector 160 used for connecting image processing system 120 with medical imaging device 101. Proximal connector 160 includes housing (or proximal hub) 502, multiple pin contact 504, printed circuit assembly (PCA) 506, contact assembly 508, coupler 512 and proximal driveshaft 514. Housing 502 provides a housing for the various components of proximal connector 160. Proximal driveshaft 514 is configured to couple with and rotate driveshaft 110 of device 101. The sensor and imager signals provided over rotating transmission cable 112 are transferred to a static, non-rotating cables via contact assembly 508, which includes tri-axial contact 509 and rotary transformer assembly 510. Coupler 512 couples contact assembly 508 to housing 502. The sensor and imager signals are then connected with PCA 506, which includes interface circuitry and the like. Communication between image processing system 120 and PCA 506 occurs over multiple pin contact 504.

Figure 5B:
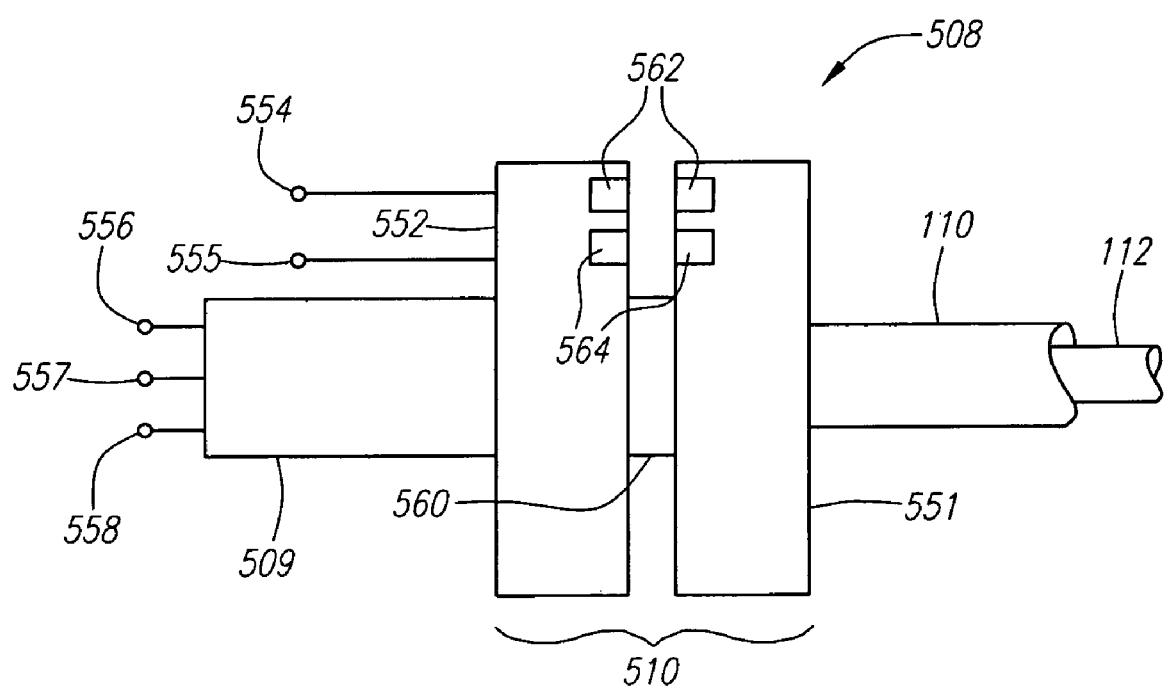
FIG. 5B depicts a schematic view of an exemplary embodiment of a contact assembly.

FIG. 5B depicts an exemplary embodiment of a contact assembly 508 including tri-axial contact 509 and rotary transformer assembly 510. In this embodiment, assembly 510 includes two concentric portions 551 and 552. Transformer portion 551 is configured to rotate with driveshaft 110 while portion 552 remains fixed. In this embodiment, the imager output signal is provided differentially over cables 554 and 555 and are transmitted over rotary junction 560 using capacitive couplings 562 and 564. The output signal from sensor 106 can be provided over cables 556 and 557, while the shield portion of transmission cable 112 can be coupled with a ground source via wire 558. Transmission cable 112 is coupled with cables 556-558 using physical rotary contacts within tri-axial contact 509. Examples of physical rotary contacts can include a combination of a spring coupling or metallic brush with a conductive shell and the like.

Figure 6:
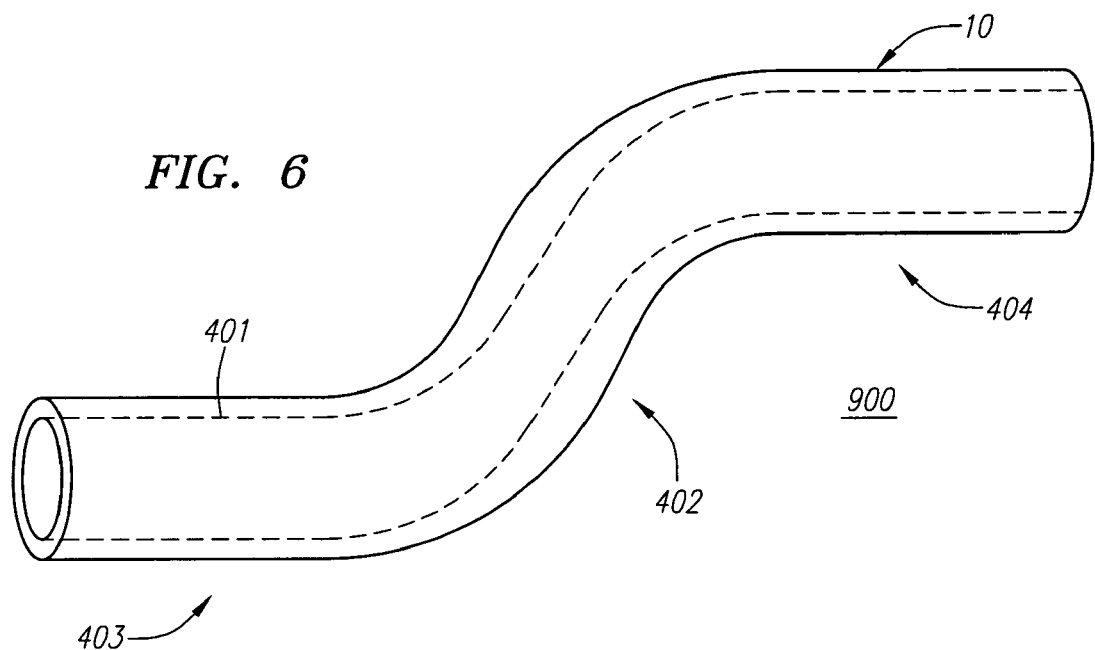
FIG. 6 depicts an exemplary reconstructed 3D image of a body lumen generated with the medical imaging system.

FIG. 6 depicts an exemplary reconstructed image 900 of blood vessel 10 created with medical imaging system 100. Here, the three dimensional structure of vessel 10 has been reconstructed based on the positional and orientation information provided by image acquisition system 102. In this image, blood vessel 10 includes a semi-vertical portion 402 surrounded by two horizontal portions 403 and 404. Detection of the border between the fluid in vessel 10 and the vessel tissue allow depiction of the inner wall 401 of vessel 10. In this instance, it can be seen that vessel 10 has a narrow region within semi-vertical segment 402, which could be caused by a lesion, occlusive plaque or other vessel defects.

Figure 7:
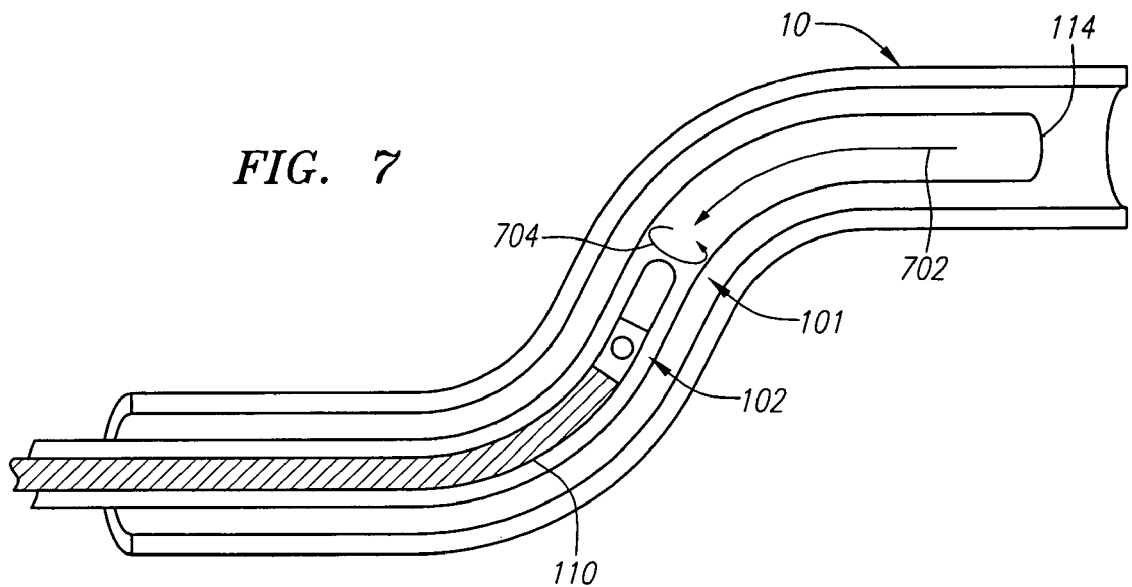
FIG. 7 depicts a cross-sectional view of a body lumen with an exemplary embodiment of the medical imaging device located therein.

Preferably, in order to create a 3D reconstruction of a desired length of a body lumen, the user uses medical imaging device 101 in a pull back procedure. FIG. 7 depicts an exemplary embodiment of medical imaging device 101 located within a body lumen during a pull back procedure. Here, medical device 101 is advanced into the desired portion of the body lumen, which is first located using an external imaging technique such as X-ray or floroscopy and the like. Once in position, driveshaft 110 is rotated within elongate tubular member 114 pulled back in direction 702 to allow imaging device 104 to image the interior of the vessel. During this pull back sequence, sensor. 106 detects the three dimensional position and orientation of the image acquisition system 102 and outputs a signal to image processing system 120. Image processing system 120 correlates the image information provided by imager 104 with the position and orientation information provided by sensor 106 to accurately reconstruct the 3D vascular structure.

Figure 8:
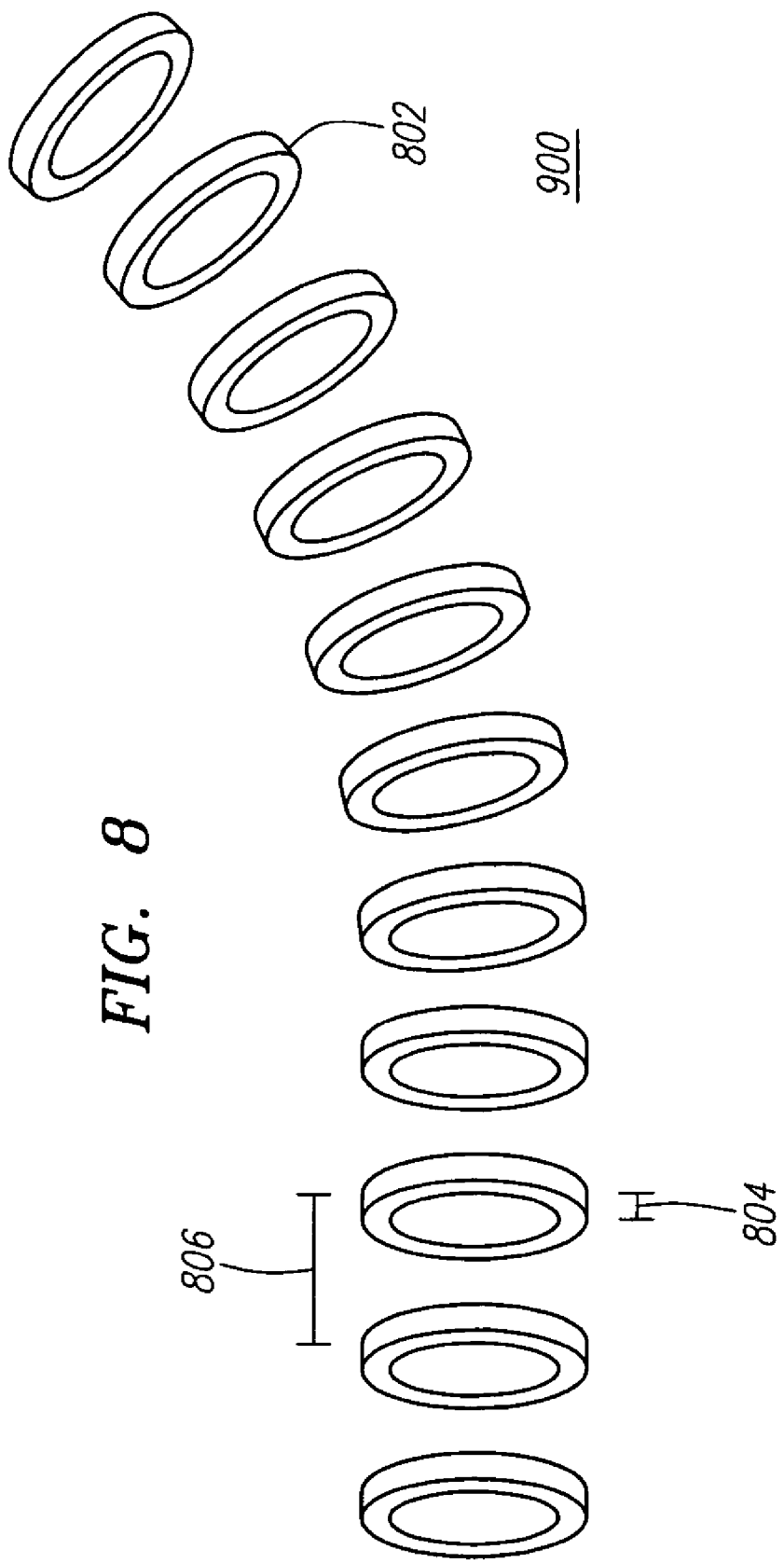
FIG. 8 depicts another exemplary reconstructed 3D image of a body lumen generated with the medical imaging system.

In one exemplary embodiment of medical imaging system 100, the image acquisition system 102 is configured to image the body lumen as a series of cross-sections during the pull back procedure. FIG. 8 depicts an exemplary image 900 having a sequence of cross-sectional images 802. Each cross-sectional image 802 is placed within image 900 using position and orientation information measured with the aid of sensor 106 during imaging of the respective cross-section 802. This position and orientation information allows each cross-section 802 to be merged or integrated with other cross-sections 802 three-dimensionally. In this embodiment, the body lumen is under-sampled and the length 804 of each cross-section 802 is less than the distance 806 between successively imaged cross sections 802. Imaging software can be used by image processing system 120 to recreate continuous borders between cross-sections 802 to represent the walls of vessel 10 if desired.

System 100 can also be readily configured to over-sample the lumen and reconstruct 3D image 900 of blood vessel 10 using overlapping cross-sections 802 where the length of each cross-section 802 is greater than the distance between each successively imaged cross-section 802. In this case, the imaging data in the overlapping region can be selected based on quality parameters, averaged together or combined with any signal or image processing technique suitable for the needs of the application.

It should be noted that conventional pull back imaging techniques require the imager to be pulled back automatically and at a metered pace. This is in order to guarantee-proper spatial positioning of each image segment with respect to another. System 100 can be configured for metered pull back at any desired rate. In one embodiment, system 100 is configured for metered pull back at a rate of 0.5 mm/second for up to 5 minutes. In another embodiment, system 100 can be configured to allow any variable, non-metered rate of pull back, and can even allow reversal of the direction of motion, i.e., switching from pull-back to push-forward. This is because each set of imaging data has position and orientation data associated therewith. Using the position and orientation data, image processing system 120 is able to place or align each set of imaging data in the proper location without dependence on a metered pull back rate.

Figure 9:
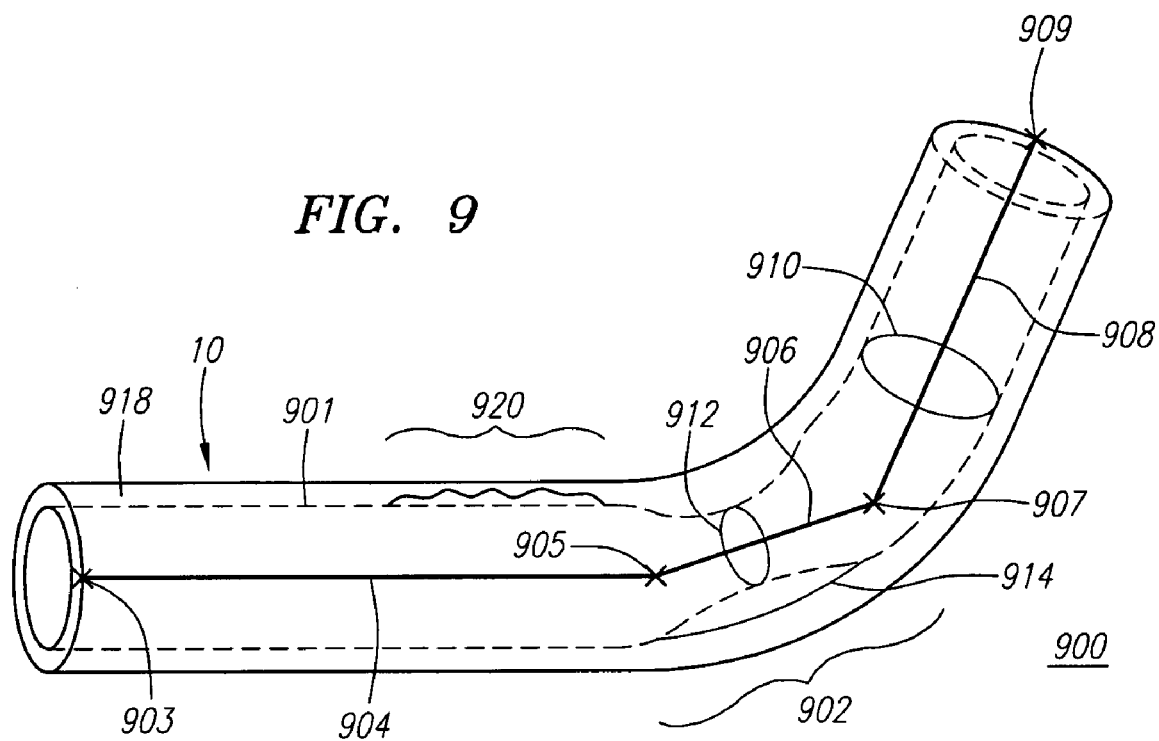
FIG. 9 depicts another exemplary reconstructed 3D image of a body lumen generated with the medical imaging system.

FIG. 9 depicts an exemplary embodiment of a 3D image 900 of vessel 10, reconstructed with medical imaging system 100. This exemplary image illustrates a few of the many capabilities advantages provided to the user by imaging system 100. In image 900, vessel 10 includes an inflamed diseased region 902. Image 900 is preferably displayed on a GUI 122 which allows the user to interact with image 900 using optional software tools incorporated with image processing system 120. For instance, the user can interactively measure the distance between any two points on vessel 10, such as the distance 904 between one end of the imaged vessel 10 and the base of diseased region 902. To do so, the user would position reference markers 903 and 905 on image 900 using an interaction device such as a keyboard, mouse and the like. The user could then request the measurement of distance 904 between points 903 and 905, which, based on the information provided to image processing system 120, can then be calculated.

Similarly, the user is able to measure any other desired distance, such as distance measurement 906 across region 902 between points 905 and 907 and distance measurement 908 from the opposite base of region 902 to the end of the imaged vessel 10 between points 907 and 909. The user can also measure cross sectional areas by positioning a cross-sectional cursor or marker in the desired position. For instance, the user can measure the cross-sectional area of a healthy region of vessel 10 by placing cross-sectional marker 910 as shown here. The user could then compare the percent stenosis between position 910 and the cross-sectional area of vessel 10 in diseased region 902 by placing the cross-sectional marker in position 912. Furthermore, the user could measure the surface area of vessel 10 in a given location using a surface area marker. For instance, placement of surface area marker in position 914 over inflamed region 902 allows a calculation of the tissue surface area of diseased region 902.

3D image 900 can also display images of the interior of the lining or wall 918 of vessel 10. For instance, images showing the presence of occlusive or vulnerable plaque within wall 918 in region 920 can be displayed. The distance by which plaque region 920 extends into wall 918 can then be measured and the specific type of plaque present can be diagnosed accordingly.

Figure 10:
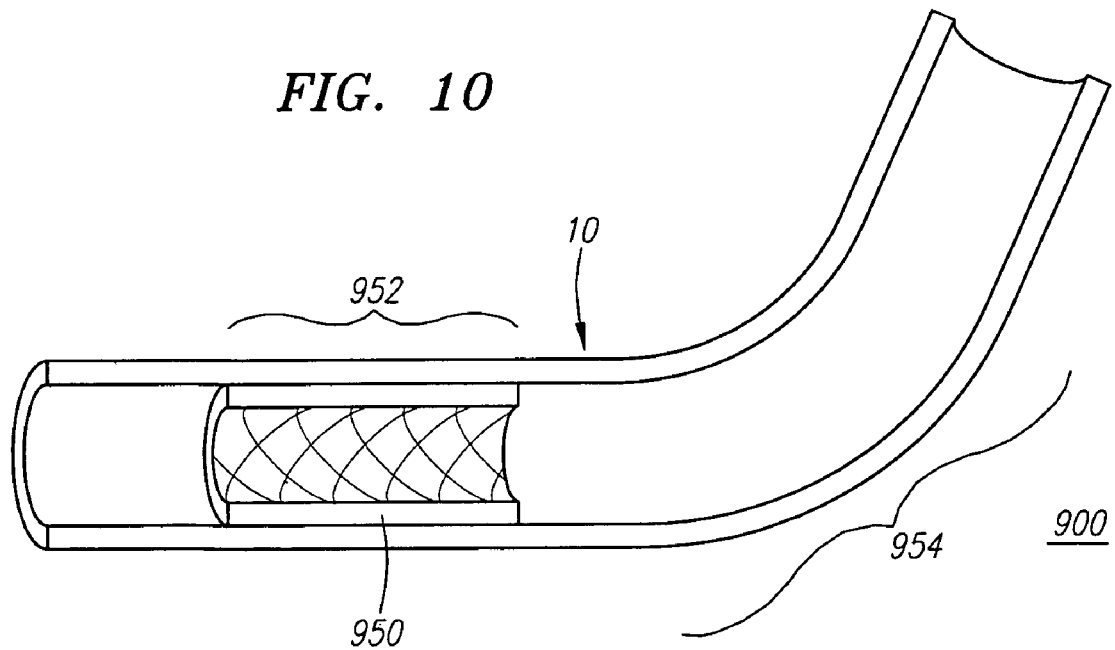
FIG. 10 depicts another exemplary reconstructed 3D image of a body lumen generated with the medical imaging system.

FIG. 10 depicts another exemplary embodiment of 3D image 900. Here, the user has selectively chosen to display only a longitudinal cross-section of vessel 10 using the software tools of image processing system 120. Image 900 is taken after a stent deployment procedure where stent 950 is placed over occlusion 952. Medical imaging device 101 is preferably configured to slide within stent 950 to allow imaging of the vessel without disturbing the placement of stent 950. Using this image 900, the placement of stent 950 can be verified to be over diseased region 952 and not within curved region 954 of vessel 10.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A medical imaging system, comprising:
    an elongate medical device configured to be inserted into a blood vessel, the elongate medical device having an inner lumen located therein, wherein the inner lumen has an enclosed distal end;
    a flexible driveshaft having a distal end;
    a rotating image acquisition system insertable into the inner lumen of the elongate medical device and coupled to the distal end of the flexible drive shaft, the image acquisition system comprising an imager and a position and orientation sensor, the imager configured to image the blood vessel and the position and orientation sensor configured to detect the position and orientation of the image acquisition system in three dimensional space within the blood vessel, the image acquisition system further configured to output at least one output signal, wherein the flexible driveshaft and the image acquisition system are slidably received within the inner lumen of the elongate medical device, wherein the position and orientation sensor is disposed distal to the imager, and wherein the position and orientation sensor is configured and arranged to rotate with the imager; and
    an image processing system communicatively coupled with the image acquisition system and configured to process the at least one output signal and create a three dimensional image of the blood vessel based on the at least one output signal.

2. The system of claim 1, wherein the image acquisition system is configured to detect the yaw and pitch of the acquisition system.

3. The system of claim 1, wherein the position and orientation sensor is active.

4. The system of claim 1, wherein the position and orientation sensor is passive.

5. The system of claim 4, wherein the image acquisition system comprises an ultrasound transducer.

6. The system of claim 4, wherein the image acquisition system comprises an optical imager.

7. The system of claim 1, wherein the image acquisition system is configured to output a first output signal usable to generate an image of the internal lumen and a second output signal usable to determine the position and orientation of the image acquisition system.

8. The system of claim 7, wherein the image acquisition system comprises:
    an ultrasound transducer configured to output the first output signal; and
    the position and orientation sensor configured to output the second output signal.

9. The system of claim 8, further comprising a generally cylindrical housing coupled to the distal end of the driveshaft, wherein the ultrasound transducer and the position and orientation sensor are both housed within the housing, and the housing has an opening aligned with the ultrasound transducer.

10. The system of claim 9, wherein the housing has a rounded distal end.

* * * * *

UNITED STATES PATENT AND TRADEMARK OFFICE
CERTIFICATE OF CORRECTION

PATENT NO. : 7,621,874 B2  Page 1 of 1
APPLICATION NO. : 11/012663
DATED : November 24, 2009
INVENTOR(S) : Romley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 946 days.

Signed and Sealed this

Twenty-sixth Day of October, 2010

David J. Kappos
*Director of the United States Patent and Trademark Office*